United States Patent [19]
Randklev

[11] Patent Number: 4,871,261
[45] Date of Patent: Oct. 3, 1989

[54] VACUUM MIXING APPARATUS FOR DENTAL MATERIALS

[75] Inventor: Ronald M. Randklev, White Bear, Minn.

[73] Assignee: Minnesota Mining and Manufacturing Company, St. Paul, Minn.

[21] Appl. No.: 251,543

[22] Filed: Sep. 29, 1988

[51] Int. Cl.$^4$ .................................. B01F 13/06
[52] U.S. Cl. ................................ 366/139; 366/602
[58] Field of Search ............... 366/139, 602, 600, 208, 366/209, 210, 218, 219, 237

[56] References Cited

U.S. PATENT DOCUMENTS

| | | | |
|---|---|---|---|
| 1,530,212 | 3/1925 | Solon . | |
| 1,774,258 | 8/1930 | English . | |
| 2,382,978 | 8/1945 | Curry | 206/47 |
| 2,527,992 | 10/1950 | Greenberg | 206/47 |
| 3,336,669 | 8/1967 | Kramer | 32/15 |
| 3,337,039 | 8/1967 | Knittel et al. | 206/47 |
| 3,347,530 | 10/1967 | Platt | 366/602 |
| 3,415,361 | 12/1968 | Adams, Jr. et al. | 206/47 |
| 3,559,961 | 2/1971 | Bergendal | 259/72 |
| 3,640,510 | 2/1972 | Lea | 366/139 |
| 3,749,371 | 7/1973 | Folkenroth | 366/602 |
| 3,815,115 | 6/1974 | Inque | 366/602 |
| 4,358,028 | 11/1982 | Chiquiar-Arias | 222/107 |
| 4,664,257 | 5/1987 | Nilson | 206/219 |

OTHER PUBLICATIONS

"Some Aspects of Vacuum Mixing of Composite Resins and its Effect on Porosity", Quintessence International, No. 7, Report No. 1778 (Jul. 1979, pp. 1–5).

Primary Examiner—Robert W. Jenkins
Attorney, Agent, or Firm—Donald M. Sell; Walter N. Kirn; James D. Christoff

[57] ABSTRACT

A mixing apparatus includes a capsule having two or more segments which nay be uncoupled or opened for adding additional ingredients to a pre-dosed ingredient just prior to the mixing operation. The capsule includes a port which is brought into registration with a vacuum port and an adjacent passageway carried by an arm of a dental amalgamator when the capsule is mounted on the arms, and sealing engagement of the perimeter of the capsule port with the port carried by amalgamator arm enables the establishment of sub-atmospheric pressure conditions within the capsule during the mixing operation. Optionally, the ingredients are mixed in a disposable ampule carried within the capsule, and vacuum conditions are established both internally and externally of the ampule for preventing unintentional compression of the ampule. The apparatus is particularly useful for mixing materials which, after mixing, have a consistency ranging from a light cream to a thick, viscous paste.

15 Claims, 2 Drawing Sheets

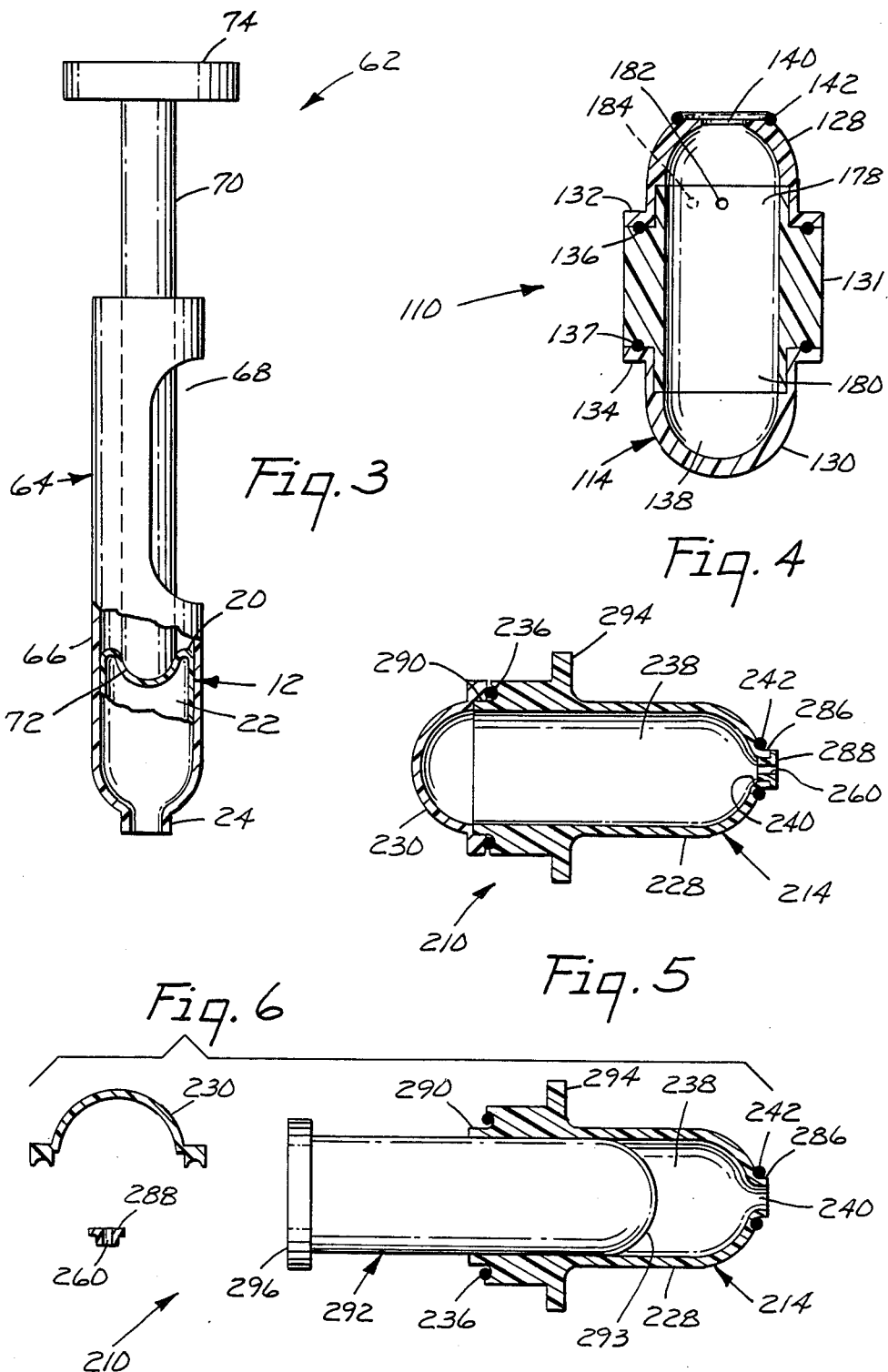

VACUUM MIXING APPARATUS FOR DENTAL MATERIALS

BACKGROUND OF THE INVENTION

1. Field of the Invention

This invention relates to vacuum mixing apparatus especially useful for mixing dental cements, liners, bases, composite restoratives, sealants and bone augmentation materials.

2. Description of the Related Art

The efficacy of mechanical mixing of dental materials such as restoratives is, in general, well recognized to those versed in the art. Handling and strength properties of mechanically mixed materials are improved by virtue of a more complete dispersion of the ingredients or components in one another. Since a large number of dental offices are provided with dental triturators or amalgamators, it is consequently efficient and convenient for the practitioner to use such mixing apparatus for combining ingredients other than amalgams.

For example, mechanically mixed pastes formed from powder and liquid components are typically characterized as exhibiting a greater fluidity and somewhat lower visual opacity than the same pastes prepared by hand mixing or spatulation. Mechanical mixing of a liquid and powder, when compared to hand mixing, normally results in a more thorough wetting of the powder particles which reduces air space between adjacent particles and improves consolidation of the paste.

In addition, the effective working time or placement time of mechanically mixed reactive materials is greater than the working time of hand spatulated materials since the time required for mechanical mixing is significantly shorter than the time normally required for mixing the ingredients by hand. Mechanical mixing also provides added convenience, mix reliability and reproducibility and saves considerable time.

Recently, efforts have been directed toward improving the aesthetic qualities of light curable ionomer restoratives. It has been found that the translucency and surface smoothness of such restoratives can be improved by mechanically mixing the ingredients under vacuum to remove opacifying air bubbles and voids. During one study, vacuum mixing of resin composites was found to reduce porosity in the material by about 90 percent and increase the diametral tensile strength by 11.5 percent. For the dentist or dental assistant, such a reduction in porosity facilitates the establishment of polishable, smooth surfaces on the restorative with improved resistance to staining, and the number of potential plaque propagation sites is correspondingly reduced. Moreover, a reduction in opacity leads to a greater depth of cure and an improved cosmetic appearance.

However, conventional vacuum mixing apparatus is not entirely satisfactory when used in dental offices. Conventional apparatus is often provided with a vacuum hose which must be manually connected to the mixing container before the mixing operation, and then disconnected from the container in order to facilitate access to the mixed materials, and such a procedure is somewhat time consuming. In addition, the expense of apparatus dedicated to vacuum mixing is not an insignificant sum.

SUMMARY OF THE INVENTION

In accordance with the present invention, a sub-atmospheric mixing apparatus includes a capsule having structure defining an internal compartment adapted to contain a quantity of ingredients, a holding mechanism for releasably supporting the capsule, and means for oscillating the holding mechanism in order to mix the ingredients in the capsule. A passageway communicates with a source of vacuum and terminates at a first port adjacent the holding mechanism, and the capsule has a second port which is in communication with the compartment. The second port is in communication with the first port when the capsule is supported by the holding mechanism in order to enable the source of vacuum to establish sub-atmospheric conditions in the compartment.

The invention may be practiced by effecting an inexpensive modification of a conventional amalgamator, and thus is readily affordable for the majority of dental offices. A reliable vacuum may be drawn upon the mixing compartment as soon as the capsule is loaded onto the amalgamator without the need for manually coupling a vacuum hose or other type of device to the capsule.

BRIEF DESCRIPTION OF THE DRAWINGS

FIG. 3 is a reduced, side elevational view with parts broken away in section of a dispenser for expelling ingredients from the ampule of FIG. 1 subsequent to the mixing operation;

FIG. 4 is a side cross-sectional view of a mixing capsule in accordance with another form of the invention;

FIG. 5 is a side cross-sectional view of a mixing capsule constructed in accordance with another embodiment of the invention; and FIG. 6 is a view similar to FIG. 5 except that a cover and a cap of the capsule have been removed and a plunger inserted into a mixing compartment of the capsule in order to dispense the ingredients therein through an outlet opening.

DESCRIPTION OF THE PREFERRED EMBODIMENTS

Figure 2:
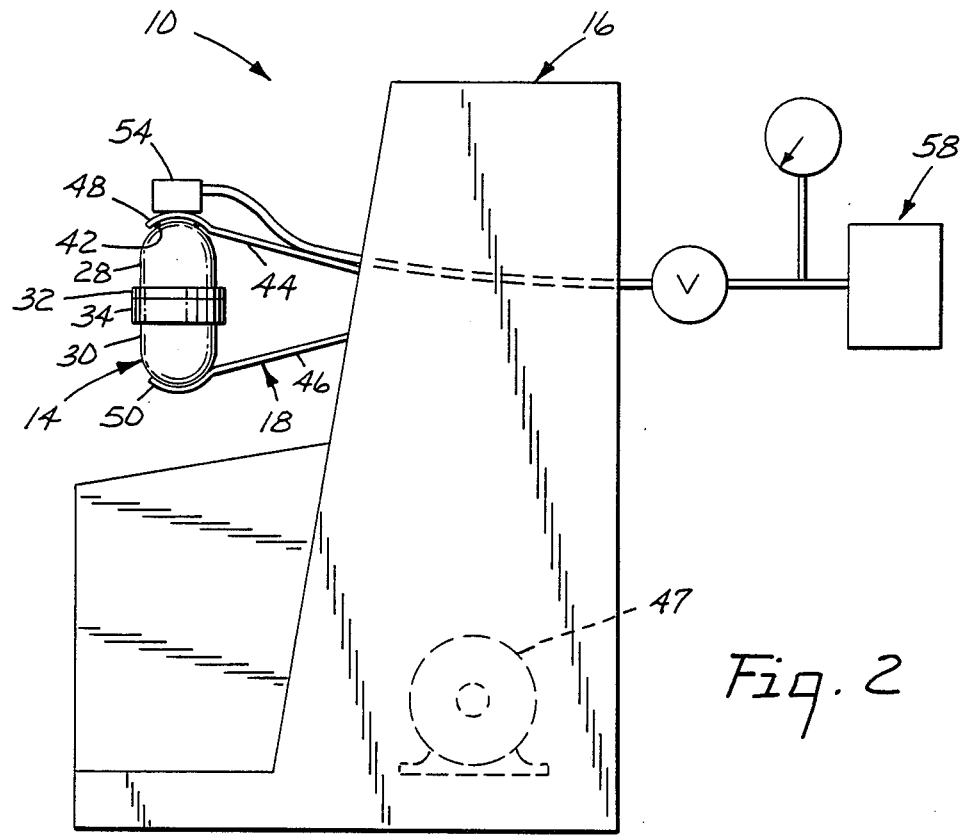
FIG. 2 is a reduced, elevational view in partially schematic form, illustrating the capsule, the amalgamator and source of vacuum for establishing subatmospheric pressure conditions within the capsule and ampule of FIG. 1.
Figure 1:
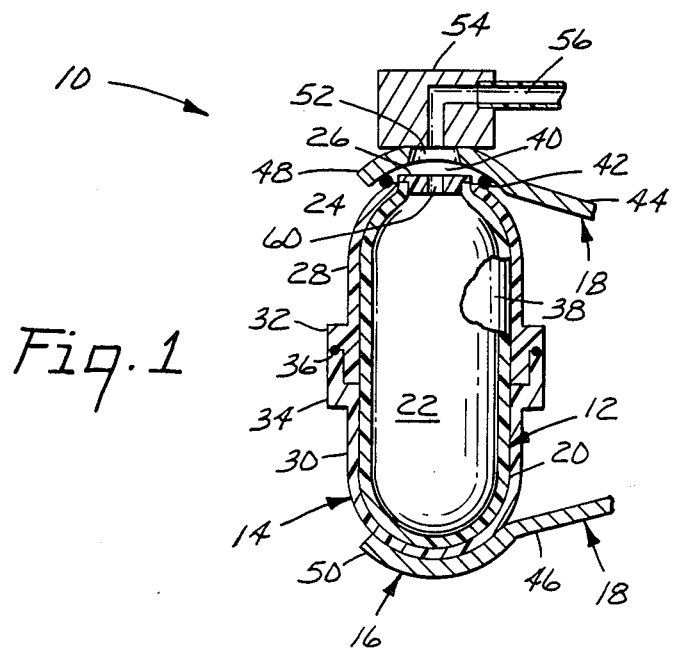
FIG. 1 is a fragmentary, side cross-sectional view of a mixing capsule and disposable ampule which are supported by arms of a dental amalgamator in accordance with one embodiment of the present invention, with parts of the ampule broken away to show a compartment of the capsule.

A vacuum mixing apparatus in accordance with one embodiment of the present invention is illustrated in FIGS. 1 and 2 and is broadly designated by the numeral 10. The apparatus 10 includes a disposable insert or ampule 12, a rigid capsule 14 for supporting the ampule 12, and an amalgamator 16 having a holding mechanism 18 that is adapted to carry the capsule 14 during the mixing operation while establishing vacuum conditions within the capsule 14 and ampule 12.

More particularly, the ampule 12 has unitary, flexible wall portions 20 that present a generally, overall oval-shaped configuration and which define a single, internal mixing chamber 22. One end section of the elongated ampule 12 tapers to a somewhat cylindrical, protruding neck 24 that defines an outlet opening which is initially closed by a friction-fit stopper 26.

Preferably, the chamber 22 is pre-dosed with a single component or ingredient, and other reactive components or ingredients are added to the chamber 22 just prior to the mixing operation. The stopper 26 is removed from the neck 24 to add additional ingredients to the chamber 22 by means of a dropper or syringe. Alternatively, the stopper 26 may be of a composition suitable for enabling protrusion of a syringe needle through the stopper 26 and directly into the chamber 22 for introduction of the additional ingredients as desired.

The capsule 14, as best illustrated in FIG. 1, includes a first rigid capsule segment 28 and a second rigid capsule segment 30. The segments 28, 30 present enlarged flange portions 32, 34 respectively adapted for telescopic, sliding fit within one another in order to couple or uncouple the segments 28, 30 as desired. An -ring 36 is disposed in an annular groove extending around the flange portion 32 in order to establish a gas seal between flange portions 32, 34 when the capsule segments 28, 30 are coupled together.

The capsule segments 28, 30 together define a generally oval-shaped mixing compartment 38 which, in this embodiment, is occupied by the ampule 12. The internal walls of the capsule 14 defining the compartment 38 are complemental in configuration to the external wall portions 20 of the ampule 12 in order to snugly hold the ampule 12 and prevent the latter from substantial movement relative to the capsule 14 during the mixing operation.

A longitudinally outermost end region of the first capsule segment 28 has structure defining an outermost or endmost circular port 40, as well as a circular groove which carries an -ring 42 that circumscribes the port 40. The neck 24 of the ampule 12 extends into the opening or port 40 although other constructions are, of course, possible.

The single-use ampule 12 may be made of any one of a number of flexible materials such as polyethylene, polypropylene or a material sold under the trademark "Surlyn" and available from DuPont. Other inexpensive, flexible materials which are impermeable and unreactive with the ingredients or components may also be utilized.

On the other hand, the capsule 14 is reuseable and is preferably constructed of somewhat more rigid materials in order to minimize the possibility of damage to the thin, flexible wall portions 20 of the ampule 12 during the mixing operation. The capsule 14 may be made of materials such as acrylonitrile butadiene styrene ("ABS"), and may be machined or injection molded. The ampules 12 may be of various sizes, and thus it is desirable to provide matching capsules 14 for each of the various ampules 12 by dimensioning the thickness of the capsule walls to ensure, in each instance, that the ampule 12 is substantially immovable relative to the capsule 14 and yet the capsule 14 is snugly received in the holding mechanism 18 without adjustment of the latter.

The holding mechanism 18, as shown in FIGS. 1 and 2, includes two arms 44, 46 that are somewhat resiliently biased toward one another. A motor 47 within a casing of the amalgamator is operable to oscillate the arms 44, 46 together in repetitive, quick vertical motions when the amalgamator 16 is activated to mix ingredients within the ampule 12. An end portion 48, 50 of each arm 44, 46 has a concave, generally semi-spherical shape which matches the external configuration of the end regions of capsule 14.

The end portion 48 of the arm 44, as shown in FIG. 1, has a port 52 that is in registry and communication with the capsule port 40 and which is surrounded by the O-ring 42 when the capsule 14 is placed in the holding mechanism 18. A fitting 54 carried by the end portion 48 has structure defining an internal vacuum passageway 56 which communicates with the port 52 and which is operatively coupled to a source of vacuum 58 (FIG. 2). In practice, the fitting 54 may be rigid and securely coupled to the end portion 48, and a length of flexible tubing may be connected to the arm 44 to establish the aforementioned passageway 56 interconnecting port 52 and vacuum source 58.

Referring again to FIG. 1, the stopper 26 within the neck 24 of the ampule 12 has a small, internal channel 60 which communicates the mixing chamber 22 and the vacuum passageway 56. Alternatively, the stopper 26 may be made of a material which is readily permeable to the flow of gases and yet which substantially precludes escape of ingredients from the chamber 22 during the mixing operation.

As the capsule 14 is placed in the holding mechanism 18, the ports 40, 52 are brought into registry with each other since the configuration of the end portions 48, 50 of the amalgamator arms 44, 46 is complemental to the shape of respective, external end regions of the capsule 14. Thus, the orientation of the capsule 14 relative to the arms 44, 46 is essentially identical each time the capsule 14 is loaded onto the amalgamator 16. Sub-atmospheric pressure conditions within the chamber 22 are therefore automatically established during each separate mixing operation without effort or attention from the dentist or dental assistant.

In this regard, it is to be noted that subatmospheric pressure conditions are established in the chamber 22 as well as the small space in the compartment 38 between the capsule 14 and the ampule 12. Consequently, the relatively thin, flexible wall portions 20 of the ampule 12 normally do not shift inwardly under the influence of external pressures during the mixing operation. Optionally, grooves or channels formed in internal walls of the capsule 14 defining the compartment 38 may be provided to promote the establishment of a vacuum in substantially all areas surrounding the ampule 12.

A dispenser 62 for the ampule 12 is illustrated in FIG. 3 and includes a central body 64 presenting a somewhat cylindrical barrel 66 with a side opening 68. A plunger 70 is movable relative to the body 64 and presents a rounded tip 72 as well as an enlarged thumb button 74 remote from the tip 72.

As soon as the capsule 14 has been shaken by the arms 44, 46 of the amalgamator 16 for a sufficient length of time, the capsule segments 28, 30 (FIG. 1) are separated from each other and the ampule 12 is removed from the capsule compartment 38. Subsequently, the stopper 26 is removed from the neck 24 and the ampule 12 is inserted through the side opening 68 of the dispenser 62 and then shifted toward the position generally shown in FIG. 3.

Next, the plunger 70 is shifted by hand relative to body 64 to bring the rounded tip 72 in contact with an end section of the ampule 12 remote from the neck 24. Continued pressure on the plunger 70 folds the wall portions 20 inwardly to expel substantially all of the contents within the chamber 22 through the neck 24

(and an opening formed in the end of the barrel 66) for delivery directly to an application site. As an alternative, the mixed contents of the ampule 12 may instead be dispensed by compressing the wall portions 20 between the thumb and forefinger.

The O-ring 42 as shown in FIG. 1 may instead be carried by the arm 44 of the amalgamator 16 in order to simplify the construction of the capsule 14 and decrease the likelihood of unintentional loss of the O-ring 42. It is preferable, however, that the port 52 is associated with the upper arm 44 of the holding mechanism 18 so that the stopper 26 remains in view of the user.

The embodiment of the invention that is shown in FIG. 4 includes an apparatus 110 which comprises a capsule 114 that has a first capsule segment 128, a second capsule segment 130 remote from the first capsule segment 128, and a third capsule segment 131 intermediate and interconnecting the segments 128, 130. The capsule segments 128, 130 have enlarged, somewhat cylindrical flange portions 132, 134 that telescopically interconnect with reduced, cylindrical flange portions 135, 135 of the capsule segment 131, and O-rings 136, 137 are disposed within annular grooves in the juncture between adjacent capsule segments in order to seal an internal mixing compartment 138 against the intrusion of atmospheric air.

The capsule 114 has an endmost, circular port 140 that is surrounded by an O-ring 142. As the capsule 114 is loaded onto a holding mechanism of a dental amalgamator similar to the amalgamator 16 shown in FIGS. 1 and 2, the port 140 comes into registration and communication with a vacuum port formed in an end portion of an arm of the amalgamator, in essentially similar manner to the embodiment illustrated in FIGS. 1 and 2. In this instance, however, the ingredients of the composition or preparation to be mixed are placed directly into the mixing compartment 138 and a disposable insert, such as ampule 12, is not employed.

Preferably, the central capsule segment 131 has opposed, cylindrical projections 178, 180 that are slidingly received in capsule segments 128, 130 respectively. I addition, a hole 182 is formed in the cylindrical projection 178, and a similarly sized hole 184 is provided in the side walls of the first capsule segment 128.

The first capsule segment 128 is rotatable relative to the third capsule segment 131 from the position which is shown in FIG. 4 wherein the holes 182, 184 are unaligned, and toward another orientation wherein the holes 182, 184 are in registration with each other. As a consequence, a syringe or other device may then be utilized to introduce additional ingredients into the mixing compartment 138 through holes 182, 184 before the mixing operation is undertaken. After introduction of the desired reactive components or ingredients to the compartment 138, capsule segment 128 is rotated relative to capsule segment 131 to bring the holes 182, 184 out of alignment relative to each other and substantially prevent the ingredients from escaping the compartment 138. An O-ring (not shown) surrounds hole 184 and contacts capsule segment 131 to substantially preclude leakage of gases therepast when the holes 182, 184 are unaligned.

During the mixing operation, O-rings 136, 137 and 142 are operable to enable sub-atmospheric pressure conditions to be established within the mixing compartment 138. Since walls of the capsule 114 are somewhat rigid, the mixed composition or preparation is withdrawn from the capsule 114 subsequent to the mixing operation by separating two of the three capsule segments 128, 130, 131 from each other and thereafter using a spatula or other tool to remove the mixture.

The mixing apparatus 210 that is illustrated in FIGS. 5 and 6 in accordance with another embodiment of the present invention includes a mixing capsule 214 that is somewhat similar to capsule 114 in that the ingredients to be mixed are placed directly within a compartment 238 of the capsule 214 without the use of an insert or ampule. However, the capsule 214 has a first and second capsule segment 228, 230, and the first capsule segment 228 is substantially larger than the second capsule segment 230 which is in the nature of a removable cover.

In more detail, the first capsule segment 228 is formed to present an outwardly projecting, cylindrical neck 286 which has an internal, central passage or port 240 (FIG. 6) and which is surrounded by an O-ring 242. A friction-fit stopper 288 is removably received in the port 240 as shown in FIG. 5, and the stopper 288 has a central, axially extending channel 260 in communication with the mixing compartment 238.

The first capsule segment 228 has an enlarged rear wall portion which presents an annular groove that carries an O-ring 236. The O-ring 236 sealingly engages the second capsule segment 230 when the segments 228, 230 are joined in the manner shown in FIG. 5. The first capsule segment 228 presents an outermost, generally cylindrical projection 290 that is slidibly received in the second capsule segment 230 in order to releasably hold the segments 228, 230 in the intercoupled relationship which is illustrated in FIG. 5.

Preferably, the capsule 214 is pre-dosed with a single reactive ingredient or component and additional ingredients are added to the compartment 238 immediately before the mixing operation by disconnecting the capsule segment 230 from the capsule segment 228. Next, the capsule segments 228, 230 are joined as shown in FIG. 5 and placed in a holding mechanism of a dental amalgamator in similar manner to the structure and orientation of the apparatus 10 shown in FIGS. 1 and 2. The O-ring 242 thereby engages an arm portion of the amalgamator surrounding a vacuum port and air is removed from the mixing compartment 238 through the channel 260 formed in the stopper 288, while the O-ring 236 substantially precludes leakage of atmospheric air past the joint between capsule segments 228, 230.

Once the capsule 214 has been shaken by the amalgamator for a sufficient length of time, the capsule 214 is removed from the holding mechanism. Net, the second capsule segment 230 is disconnected from the first capsule segment 228 and moved away from the latter toward a position sufficient to enable access to the mixing compartment 238 such as is shown in FIG. 6.

Subsequently, an end portion of an elongated plunger 292 is inserted into the compartment 238 and the stopper 288 is withdrawn from the port 240. The plunger 292 is then shifted in a direction along the longitudinal axis of the compartment 238 in order to expel the ingredients through port 240, preferably directly toward an application site. The plunger 292 has a rounded, forwardmost tip 293 complemental to the endmost walls defining the compartment 238 surrounding the port 240 so that substantially all of the mixed ingredients within compartment 238 are dispensed through the port 240.

Preferably, the capsule 214 is formed with a circumscribing, outwardly extending flange 294 and the rearwardmost end of the plunger 292 includes an enlarged thumb button 296. In this manner, the capsule 214 may be grasped between two fingers of the user's hand with the fingers in contact with flange 294 as the thumb of the same hand is in contact with the button 296, for shifting the plunger 292 relative to the capsule 214 in a convenient fashion while leaving the remaining hand of the user free for other tasks.

The vacuum mixing apparatus as described hereinabove is especially useful for mixing light curable materials such as dental cements, liners, bases, composite restoratives, sealants and bone and ridge augmentation materials. The vacuum mixing apparatus, however, is also useful for mixing other materials such as pharmaceuticals, medicaments and adhesives. In this regard, it should be noted that the mixing compartments of the capsules are rounded to facilitate removal of substantially all of the mixed ingredients, particularly in instances where the composition is in the form of a heavy paste.

I claim:

1. Sub-atmospheric mixing apparatus comprising:
   a capsule having structure defining an internal compartment adapted to contain a quantity of ingredients;
   a holding mechanism for releasably supporting said capsule;
   means for oscillating the holding mechanism in order to mix the ingredients in the capsule;
   a source of vacuum; and
   means defining a passageway communicating with said source of vacuum and terminating at a first port carried by said holding mechanism,
   said capsule having a second port in communication with said compartment, said second port being in communication with said first port when said capsule is supported by said holding mechanism in order to enable said source of vacuum to establish sub-atmospheric conditions in said compartment.

2. The apparatus of claim 1; and including an ampule removably received in said compartment of said capsule, said ampule having an internal, ingredient-receiving chamber in communication with said second port.

3. The apparatus of claim 2, wherein said ampule has flexible wall portions.

4. The apparatus of claim 2, wherein said ampule has structure defining an opening; and including a stopper removably received in said opening, said stopper having structure for communicating said chamber with said passageway.

5. The apparatus of claim 1, wherein said capsule has a generally oval-shaped configuration in longitudinal sectional view, and presents a longitudinally outer end region having said second port.

6. The apparatus of claim 5, wherein said holding mechanism includes an arm having a concave portion for receiving said end region of said capsule.

7. The apparatus of claim 6, wherein said structure defining said passageway is carried by said arm.

8. The apparatus of claim 6, wherein said first port is disposed in said concave portion of said arm, and wherein said second port is disposed in said end region of said capsule.

9. The apparatus of claim 1, wherein said capsule includes a first capsule segment, a second capsule segment, and means releasably coupling said first capsule segment to said second capsule segment for enabling access to said compartment.

10. The apparatus of claim 9, wherein said first capsule segment is rotatable relative to said second capsule segment when said first capsule segment is coupled to said second capsule segment, and wherein said first capsule segment and said second capsule segment each have structure defining respective holes, and wherein said hole of said first capsule segment is shifted from a position of non-alignment to a position of alignment relative to said hole of said second capsule segment when said first capsule segment is rotated relative to said second capsule segment.

11. The apparatus of claim 1; and including a dispensing plunger movable in said compartment for dispensing ingredients from said compartment.

12. The assembly of claim 1, wherein said capsule includes a first capsule segment and a second capsule segment selectively movable relative to said first capsule segment from a position closing said compartment and toward a position enabling access to said compartment; and including a plunger having a tip portion complemental in configuration to the configuration of said compartment, said tip portion being received in said compartment after said second capsule segment has been moved to said position enabling access to said compartment, said tip portion being movable in a direction generally along the longitudinal axis of said compartment in order to dispense mixed ingredients from said compartment and through said second port.

13. The apparatus of claim 12; and including structure for effectively precluding the passage of gases between said first capsule segment and said second capsule segment when said second capsule segment is moved to said position closing said compartment.

14. The apparatus of claim 12, wherein said first capsule segment includes an outwardly extending, finger engageable flange.

15. The apparatus of claim 12, wherein said plunger includes an enlarged thumb button remote from said tip portion.

* * * * *